United States Patent [19]

Sohn

[11] Patent Number: 5,309,085
[45] Date of Patent: May 3, 1994

[54] MEASURING CIRCUIT WITH A BIOSENSOR UTILIZING ION SENSITIVE FIELD EFFECT TRANSISTORS

[76] Inventor: Byung Ki Sohn, 425-4, Chung-dong, Suseong-ku, Taegu, Rep. of Korea

[21] Appl. No.: 982,002

[22] Filed: Nov. 24, 1992

Related U.S. Application Data

[63] Continuation of Ser. No. 746,738, Aug. 19, 1991, abandoned.

[30] Foreign Application Priority Data

Aug. 21, 1990 [KR] Rep. of Korea ............... 1990-12885

[51] Int. Cl.$^5$ ............................................ G01N 27/00
[52] U.S. Cl. ............................. 324/71.5; 324/158 T; 324/705; 204/403; 204/418
[58] Field of Search .................... 324/71.1, 71.5, 705, 324/713, 158 T; 204/403, 418, 153.12; 435/288, 817

[56] References Cited

U.S. PATENT DOCUMENTS

| | | | |
|---|---|---|---|
| 3,358,223 | 12/1967 | Birnstingl | 324/705 X |
| 4,233,033 | 11/1980 | Eifler et al. | 324/717 X |
| 4,374,013 | 2/1983 | Enfors | 204/153.12 X |
| 4,385,274 | 5/1983 | Shimada et al. | 324/71.6 |
| 4,490,678 | 12/1984 | Kuisl et al. | 324/438 |
| 4,513,280 | 4/1985 | Hannan et al. | 204/153.12 X |
| 4,657,658 | 4/1987 | Sibbald | 204/418 X |
| 4,789,825 | 12/1988 | Carelli et al. | 324/158 T |
| 4,812,220 | 3/1989 | Iida et al. | 204/403 |
| 4,839,000 | 6/1989 | Eddowes | 204/153.12 |

*Primary Examiner*—Kenneth A. Wieder
*Assistant Examiner*—Glenn W. Brown
*Attorney, Agent, or Firm*—Robert E. Bushnell

[57] ABSTRACT

A measuring circuit with a biosensor utilizing ion sensitive field effect transistors having a simplified structure and is advantageous to integration. The measuring circuit comprises two ion sensitive FET input devices composed of an enzyme FET having an enzyme sensitive membrane on the gate and a reference FET, and a differential amplifier for amplifying the outputs of the enzyme FET and the reference FET. The drift phenomena of the ISFETs due to the use of a non-stable quasi-reference electrode as well as the temperature dependence thereof can be eliminated by the differential amplifier consisting of MOSFETs having the same channel as the ISFETs. The ISFET biosensor and the measuring circuit can be integrated into one chip.

29 Claims, 2 Drawing Sheets

10

MEASURING CIRCUIT WITH A BIOSENSOR UTILIZING ION SENSITIVE FIELD EFFECT TRANSISTORS

This is a continuation of application Ser. No. 07/746,738 filed on Aug. 19, 1991, now abandoned.

BACKGROUND OF THE INVENTION

1. Field of the Invention

The present invention relates to a measuring circuit with a biosensor which utilizes ion sensitive field effect transistors (ISFETS).

2. Description of the Prior Art

Biosensors have been developed as a kind of chemical sensor for sensing biomaterials.

At present, biosensors are widely used in the fields of medical treatment, basic science and food engineering. As concerns for health are increased, the importance of these biosensors has also been increased.

Conventionally, for the measurement of the biomaterials such as urea, glucose and penicillin, etc., a biosensor utilizing an ion selective electrode or a gas sensing electrode has been widely and mainly used.

However, such type of biosensor has the disadvantages that it is very expensive, large in signal size, and slow in signal response as well as difficult to handle.

Since an ISFET is a semiconductor ion sensor and manufactured by an integrated circuit manufacturing process, it has numerous advantages such as: small size, easy standardization, rapid response, economic mass production, and relatively easy integration in a signal processing circuit.

The development potential of an ISFET biosensor is highly desirable and tremendously economical because as single metal such as platinum (Pt) wire can be used to substitute for a commercial reference electrode such as a reference FET (hereinafter referred to as REFET), which has been extremely difficult to be miniaturized and to be reduced in cost since the gate is not amenable to a sensing membrane even though it is capable of having the advantages as discussed above.

The conventional measuring circuit for an ISFET biosensor comprises a REFET which is not responsive to a specific biomaterial, an enzyme FET (hereinafter referred to as ENFET) which has an enzyme sensitive membrane on its gate and is responsive to the specific biomaterial, a sensed signal detecting circuit connected to the REFET and the ENFET, and a differential amplifier which amplifies differentially the output of the sensed signal detecting circuit.

However, such measuring circuit has many disadvantages because it has a complicated structure due to the numerous elements and it is difficult to miniaturize as an entire measuring system. Moreover, it is also difficult for the ISFETs and the measuring circuit to be integrated into one chip.

SUMMARY OF THE INVENTION

It is an object of the present invention to provide a measuring circuit using an ISFET biosensor which has a compact structure and is advantageous to integration.

It is another object of the present invention to provide a measuring circuit using an ISFET biosensor, which can help miniaturize the overall sensor through the integration with the sensor, to obtain high signal-to-noise ratio and greater reliability.

In order to achieve the above object, the measuring circuit using a biosensor according to the present invention, comprises two input devices employing an ENFET with an enzyme sensitive membrane on its gate surface and a REFET with no enzyme sensitive membrane; and a differential amplifier having two metal-oxide-semiconductor field effect transistors MOSFETs as the load transistors thereof, the MOSFETs having the same channel as the ENFET and REFET.

BRIEF DESCRIPTION OF THE DRAWINGS

These and other features of the present invention will now be described in detail with reference to the accompanying drawings, in which.

DETAILED DESCRIPTION OF THE PREFERRED EMBODIMENT

Figure 1:
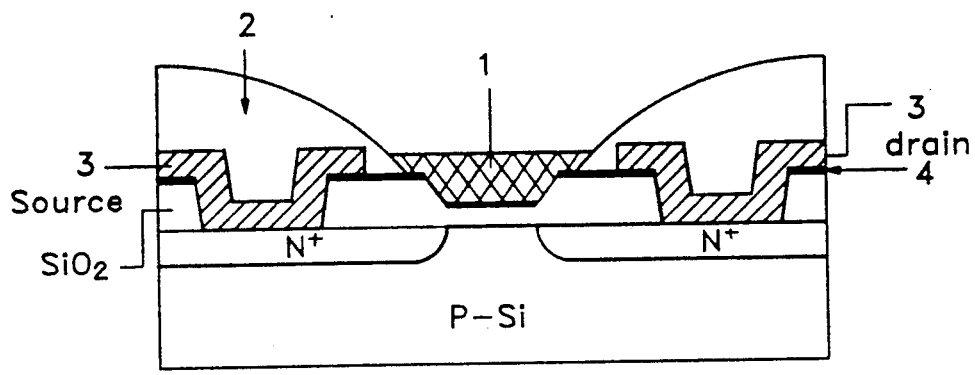
FIG. 1 shows a cross-sectional view illustrating an ISFET biosensor.

The structure of an ISFET biosensor is shown in FIG. 1.

Referring to FIG. 1, an ion sensitive membrane 4 is formed on the gate and the circumference of a metal contact 3, which acts as a drain or a source terminal of an ISFET. An enzyme sensitive membrane 1 is formed over the ion sensitive membrane 4 of the gate, so that the portion, except the enzyme sensitive membrane 1, acts as the ISFET.

In FIG. 1, a reference numeral 2 designates an electrical insulating material used to insulate the from the solution to be measured the metal contact 3.

When the ISFET biosensor is soaked in the solution, the enzyme sensitive membrane 1 reacts upon the specific biomaterial in the solution thereby resulting in the change of a biomaterial's concentration which is then converted to the change of ion concentration in the enzyme sensitive membrane.

The changing rate of the ion concentration is then sensed by the ISFET. Since the changing rate of the ion concentration corresponds to a velocity of the catalytic reaction in the membrane 1 and depends on the concentration of the biomaterial, the concentration of the biomaterial can be obtained by measuring the temporal changing rate of the potential of the ion sensitive membrane 4 based on the ion concentration change in the enzyme sensitive membrane 1.

In the meantime, for a quantitative analysis of the specific biomaterial in the solution, a reference electrode, which has the reference potential relative to the detected signals, is required. The potential of the reference electrode in the solution to be measured should be maintained as a constant one.

For the measurements of the ion concentrations in the solution, a commercial Ag/Agc1 electrode or a Calomel electrode, etc., has been developed so far. However, such types of reference electrodes are hard to be miniaturized and require troublesome maintenance and high manufacturing costs.

In case of the ISFET biosensor, a REFET and a single metal such as a Pt wire can be used as a substitute for the commercial reference electrode by adopting a differential amplifier.

Thus, the ISFET biosensor preferably consists of an enzyme FET which has an enzyme sensitive membrane on its gate and thus is responsive to a specific substrate, a reference FET which does not have an enzyme sensitive membrane and thus is not responsive to the specific substrate, and a single metal such as a Pt wire.

Figure 4:
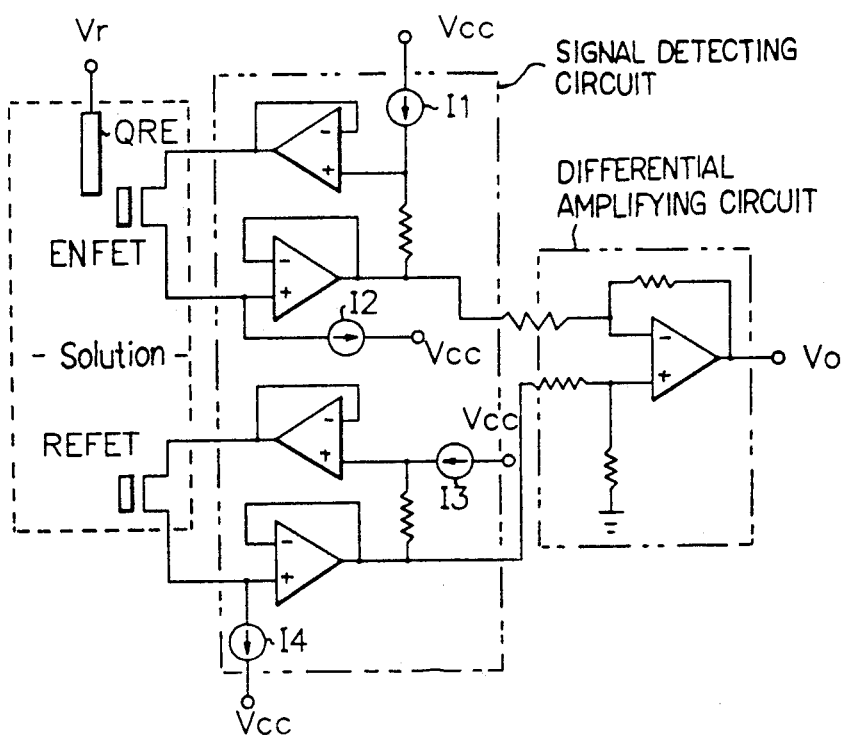
FIG. 4 shows the conventional measuring circuit using a biosensor.

FIG. 4 shows a conventional measuring circuit using a biosensor.

Referring to FIG. 4, as a quasi-reference electrode like the Pt wire is employed, the reference electrode-solution (hereinafter RE-S) interface potential can not be constant. The output voltage of an ENFET corresponds to the ion concentration of the biomaterial in the solution and the non-stable RE-S interface potential, whereas that of the output voltage REFET corresponds only to the RE-S interface potential. Thus, the change in the RE-S interface potential can be eliminated by a differential amplifying circuit and the output voltage of the differential amplifying circuit corresponds to only the measured concentration of the biomaterial.

However, as described above, such measuring circuit has numerous disadvantages in that it is difficult to miniaturize an entire measuring system due to a shear multitude of components and it is also difficult for the biosensor and the measuring circuit to be integrated into one chip.

Figure 2:
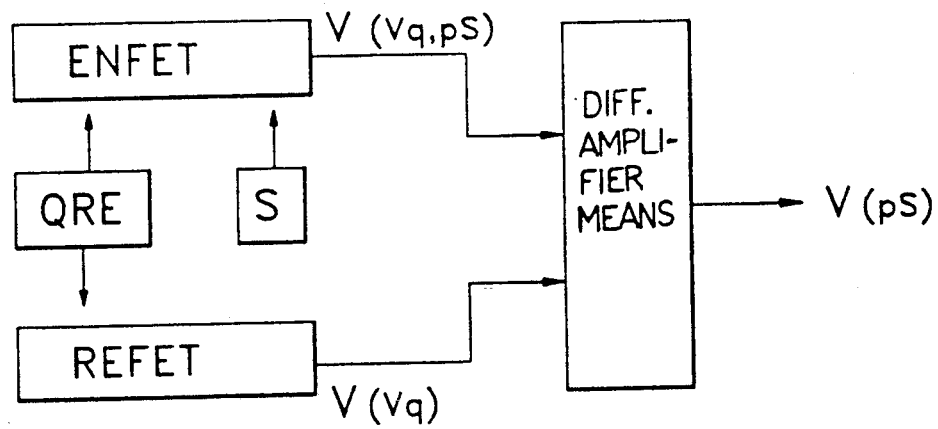
FIG. 2 shows a block diagram illustrating the measuring system using a biosensor according to the present invention.

FIG. 2 illustrates the measuring system using a biosensor according to the present invention.

Referring to FIG. 2, a quasi-reference electrode (hereinafter referred to as QRE), made of a single metal such as Pt or Au, acts as a reference electrode and has a non-stable performance in the solution. A substrate S designates a specific biomaterial to be measured.

In FIG. 2, the output voltage of an ENFET, which is an ISFET having a sensitive membrane responsive to the substrate, is a function of pS and Vq, where pS is the concentration of the material to be measured, and Vq is the non-stable potential of the solution due to the use of the QRE, so that, if the REFET is not responsive to pS, the output voltage thereof is a function of only Vq.

The output voltages of the ENFET and REFET are applied to a differential amplifying circuit. A final voltage V(pS), which is a function of pS only, can be obtained from the output of the differential amplifying circuit, as a result of the measurement of the ion concentration of the specific biomaterial.

On the other hand, as such differential amplifying circuit is employed, drift phenomena due to the non-stable potential and the temperature dependence of the QRE commonly inherent in both of the ENFET and REFET can be automatically eliminated.

Figure 3:
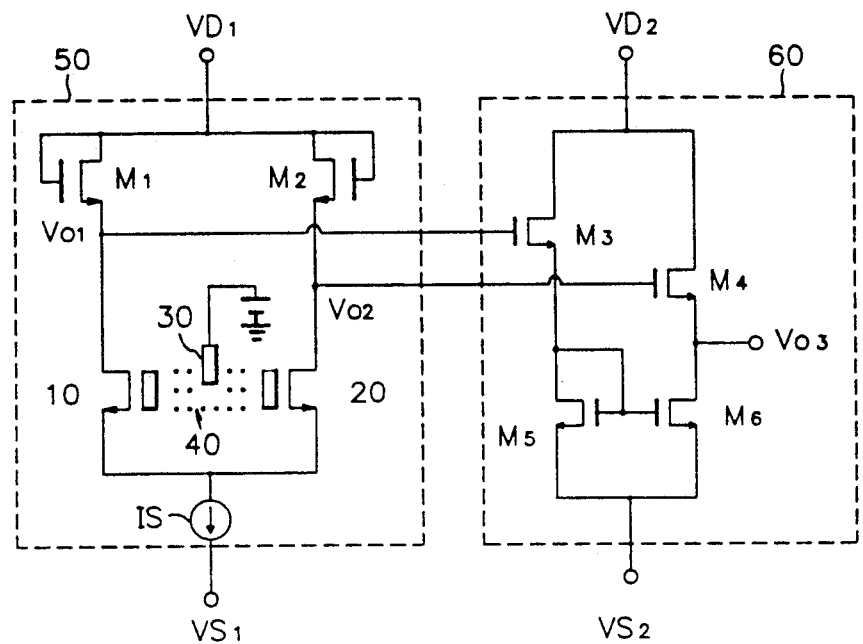
FIG. 3 shows a detailed diagram of a measuring circuit using a biosensor according to the present invention.

Referring to FIG. 3, the measuring circuit according to the present invention comprises a differential amplifying portion 50 for detecting a sensed signal and a differential to single-ended converter (hereinafter referred to as DSC) 60 for converting two differential outputs into a single output.

Two input devices of the differential amplifying portion 50 are composed of the ENFET 10 and the REFET 20 respectively, so that they can operate as a measuring circuit.

At this time, the load transistors of the differential amplifying portion 50 are composed of n-channel MOSFETs M1 and M2 of the same type as the ENFET and REFET in order to obtain a proper differential gain.

The DSC 60 is used to convert two outputs V01 and V02 of the differential amplifying portion 50 into a single output, and consists of MOSFETs M3 through M6.

Referring again to FIG. 3, constant voltage sources VD1, VD2, VS1, and VS2, and a constant current source IS are respectively supplied to the measuring circuit. The differential output (V02−V01) of the differential amplifying portion 50 corresponds to the response difference between the ENFET 10 and the REFET 20 and it can serve as a function of only the ion concentration of the biomaterial to be measured.

The differential gain of the differential amplifying portion 50 is determined by the aspect ratio (i.e., the ratio of length/width of the gate) of the MOSFETS M1 and M2, and the ENFET 10 and the REFET 20.

Two outputs V01 and V02 of the differential amplifying portion 50 are applied to the DSC 60 and converted into a single output. In detail, the output V02 of the differential amplifying portion 50 is applied to the gate of the MOSFET M4 in order to provide a source follower signal at the output V03 of the DSC 60 while the output V01 is applied to the gate of the MOSFET M3 and thus changes the gate voltage of the MOSFET M6 in order to affectuate the output V03 of the DSC.

Consequently, the output V03 of the DSC 60 corresponds to the response difference (V02−V01) between the ENFET 10 and the REFET 20 in the differential amplifying portion 50.

In the relationship between the input (V02−V01) and the output V03 of the DSC 60, the aspect ratio of the MOSFETs M5 and M6 to the MOSFETs M3 and M4 may be made as large as possible in order to obtain an excellent linear response, and thus the differential gain approaches one.

From the foregoing descriptions it will be apparent that the measuring circuit using an ISFET biosensor according to the present invention uses the ENFET and REFET as two input devices of the differential amplifying portion and performs all the analog signal processing, including the signal detection and the differential amplification in a simplified structure. Also, the measuring circuit according to the present invention consists of the ISFETs and the MOSFETs having almost the same structure as that of the ISFETs to enable the ISFET biosensor and the measuring circuit to be integrated in one chip. Furthermore, according to the present invention, the temperature dependence of the sensor itself can be eliminated by the differential amplifying portion 50. Similarly the differential gain can also be adjusted by simply varying the aspect ratio of the ISFETs. The measuring circuit according to the invention may be also applicable to ion sensors in determining inorganic ions, if the corresponding REFETs are available.

While the present invention has been described and illustrated herein with reference to the preferred embodiment thereof, it will be understood by those skilled in the art that various changes in form and details may be made therein without departing from the spirit and scope of the invention.

I claim:

1. A measuring circuit with a biosensor utilizing ion sensitive field effect transistors, comprising:
   two input devices composed of ion sensitive field effect transistors, wherein one of said ion sensitive field effect transistors is an enzyme field effect transistor having an enzyme sensing membrane on a gate surface and another one of said ion sensitive field effect transistors is a reference field effect transistor having no enzyme sensing membrane; and differential amplifier means coupled to receive output signals of said ion sensitive field effect transistors, for providing gain differentiated signals, said differential amplifier means having at least two metal-oxide-semiconductor field effect transistors, each of said metal-oxide-semiconductor field effect transistors having the same-type channel as said enzyme field effect transistor and said reference field effect transistor.

2. A measuring circuit, comprising:

two input devices composed of ion sensitive field effect transistors, wherein one of said ion sensitive field effect transistors is an enzyme field effect transistor having an enzyme sensing membrane on a gate surface and another one of said ion sensitive field effect transistors is a reference field effect transistor having no enzyme sensing membrane;

differential amplifier means coupled to receive output signals of said ion sensitive field effect transistors, for providing gain differentiated signals, said differential amplifier means having at least two metal-oxide-semiconductor field effect transistors, each of said metal-oxide-semiconductor field effect transistors having the same-type channel as said enzyme field effect transistor and said reference field effect transistor; and single-ended converter means for converting said gain differentiated signals into a measured signal representative of physical and chemical properties of a liquid of interest, said single-ended converter means comprising at least four metal-oxide-semiconductor field effect transistors having the same-type channel said enzyme field effect transistor and said reference field effect transistor.

3. The measuring circuit as claimed in claim 2, wherein the differential gain of said differential amplifier means is adjusted by varying an aspect ratio of each of said enzyme field effect transistor, said reference field effect transistor and said metal-oxide-semiconductor field effect transistors.

4. The measuring circuit as claimed in claim 2, wherein said enzyme field effect transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region and two ends extending in parallel with a surface of said ion sensitive membrane;

an enzyme sensitive membrane directly on the surface of said ion sensitive membrane over said gate region, for detecting physical and chemical properties of a liquid of interest; and a second insulating layer on the surface of said first and second metal layers, for isolating said metal layers from said liquid of interest.

5. A circuit for measuring a bio-substance concentration of a biomaterial, comprising:

a first transistor having a source region connected to a first terminal for first voltage source and an enzyme sensing membrane on a gate region, for generating a sensed signal by sensing physical and chemical properties of a biomaterial of interest;

a second transistor having a source region connected to said first terminal and a gate region, for serving as a reference electrode to provide a reference signal, said second transistor having a geometry and physical structure substantially identical to said first transistor;

a third transistor having a gate region and a drain region connected to a second terminal for a second voltage source, and a source region connected to a drain region of said first transistor, for amplifying said sensed signal to provide a first gain signal;

a fourth transistor having a gate region and a drain region connected to said second terminal, and a source region connected to a drain region of said second transistor, for amplifying said reference signal to provide a second gain signal;

a fifth transistor having a drain region connected to a third terminal for a third voltage source, and a gate region coupled to receive said first gain signal;

a sixth transistor having a drain region and a gate region connected to a source region of said fifth transistor, and a source region connected to a fourth terminal for a fourth voltage source;

a seventh transistor having a gate region connected to said source region of said fifth transistor, and a source region connected to said fourth terminal; and an eighth transistor having a drain region connected to said third terminal, a gate region coupled to receive said second gain signal, and a source region connected to a drain region of said seventh transistor at an output terminal, for providing a differentiated gain signal.

6. The circuit as claimed in claim 5, wherein said first transistor is an enzyme field-effect transistor.

7. The circuit as claimed in claim 6, wherein said second transistor is a reference field-effect transistor.

8. The circuit as claimed in claim 5, wherein each of said third, fourth, fifth, sixth, seventh and eight transistors are N-channel MOSFETs having a gate proportion substantially equivalent to said first and second transistors.

9. The circuit as claimed in claim 5, wherein said first transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region of said first transistor and a channel having two ends extending in parallel with a surface of said ion sensitive membrane;

an enzyme sensitive membrane directly on the surface of said ion sensitive membrane over said gate region of said first transistor, for detecting said physical and chemical properties of a biomaterial of interest; and a second insulating layer on the surface of said first and second metal layers, for isolating said metal layers from said biomaterial of interest.

10. A circuit for measuring a bio-substance concentration of a biomaterial, comprising:

an enzyme field-effect transistor having an enzyme sensing membrane on a gate region, for sensing physical and chemical properties of a biomaterial of interest;

a reference field-effect transistor having a geometry and physical structure substantially identical to said enzyme field-effect transistor;

differential amplifier means comprised of at least two metal-oxide semiconductor field-effect transistors having a channel region of a conductivity type substantially identical to a respective channel region of said enzyme field-effect transistor and said reference field-effect transistor, for gain differentiating output signals of said enzyme field-effect transistor and said reference field-effect transistor; and single-ended converter means comprised of at least four metal-oxide semiconductor field-effect transistors, for providing a sensed signal representative of a bio-substance concentration of said biomaterial of interest in dependence upon reception of output signals of said differential amplifier means.

11. The circuit as claimed in claim 10, wherein said enzyme field-effect transistor comprise:

a P-type semiconductor substrate having first and second diffusion regions of a N-type material separated and spaced-apart by a gate region, said first and second diffusion regions respectively defining a source region and a drain region;

a first insulating layer positioned upon one surface of said P-type semiconductor substrate;

an ion sensitive membrane positioned upon one surface of said first insulating layer;

first and second metal layers formed in a V-shape, each of said first and said second layers having a base in contact with a center of one of said source region and said drain region and a channel having two ends extending parallel to a surface of said ion sensitive membrane;

enzyme sensitive membrane positioned directly upon one surface of said ion sensitive membrane over said gate region, for detecting said physical and chemical properties of said biomaterial of interest; and a second insulating layer positioned upon the surface of said first and second metal layers, for isolating said first and said second metal layers from said biomaterial of interest.

12. A measuring circuit with a biosensor utilizing ion sensitive field effect transistor, comprising:

input means comprising ion sensitive field effect transistors, wherein one of said ion sensitive field effect transistors is an enzyme field effect transistor having an enzyme sensing membrane on a gate surface and another one of said ion sensitive field effect transistors is a reference field effect transistor having no enzyme sensing membrane; and differential amplifier means coupled to receive output signals of said ion sensitive field effect transistors, for providing gain differentiated signals, said differential amplifier means having at least two metal-oxide-semiconductor field effect transistors, each of said metal-oxide-semiconductor field effect transistors having a channel of a conductivity type substantially identical to a respective channel of said enzyme field effect transistor and said reference field effect transistor.

13. A measuring circuit, comprising:

input means comprising ion sensitive field effect transistors, wherein one of said ion sensitive field effect transistors is an enzyme field effect transistor having an enzyme sensing membrane on a gate surface and another one of said ion sensitive field effect transistors is a reference field effect transistor having no enzyme sensing membrane;

differential amplifier means coupled to receive output signals of said ion sensitive field effect transistors, for providing gain differentiated signals, said differential amplifier means having at least two metal-oxide-semiconductor field effect transistors, each of said metal-oxide-semiconductor field effect transistors having a channel of a conductivity type substantially identical to a respective channel of said enzyme field effect transistor and said reference field effect transistor; and single-ended converter means for converting said gain differentiated signals into a measured signal representative of physical and chemical properties of a liquid of interest, said single-ended converter means comprising at least four metal-oxide-semiconductor field effect transistors having the channel of the conductivity type substantially identical to the respective channel of said enzyme field effect transistor and said reference field effect transistor.

14. The measuring circuit as claimed in claim 13, wherein the differential gain of said differential amplifier means is adjusted by varying an aspect ratio of each of said enzyme field effect transistor, said reference field effect transistor and said metal-oxide-semiconductor field effect transistors.

15. The measuring circuit as claimed in claim 13, wherein said enzyme field effect transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region and two ends extending in parallel with a surface of said ion sensitive membrane;

an enzyme sensitive membrane directly on the surface of said ion sensitive membrane over said gate region, for detecting physical and chemical properties of a liquid of interest; and a second insulating layer on the surface of said first and second metal layers, for isolating said metal layers from said liquid of interest.

16. A circuit for measuring a bio-substance concentration of a biomaterial, comprising:

means for providing a reference potential across a biomaterial of interest;

a first transistor having a source region connected to a first terminal for first terminal and an enzyme sensing membrane on a gate region, for generating a sensed signal by sensing physical and chemical properties of said biomaterial of interest and said reference potential;

a second transistor having a source region connected to said first voltage source and a gate region, for serving as a reference electrode to provide a reference signal in dependence upon said reference potential, said second transistor having a geometry and physical structure substantially identical to said first transistor;

a third transistor having a gate region and a drain region connected to a second terminal for a second voltage source, and a source region connected to a drain region of said first transistor, for amplifying said sensed signal to provide a first gain signal influenced by said physical and chemical properties and by said reference potential;

a fourth transistor having a gate region and a drain region connected to said second terminal, and a source region connected to a drain region of said second transistor, for amplifying said reference signal to provide a second gain signal influenced by said reference potential;

a fifth transistor having a drain region connected to a third terminal for a third voltage source, and a gate region coupled to receive said first gain signal;

a sixth transistor having a drain region and a gate region connected to a source region of said fifth transistor, and a source region connected to a fourth terminal for a fourth voltage source;

a seventh transistor having a gate region connected to said source region of said fifth transistor, and a source region connected to said fourth terminal; and an eighth transistor having a drain region connected to said third terminal, a gate region coupled to receive said second gain signal, and a source region connected to a drain region of said seventh transistor at an output terminal, for providing a differentiated gain signal.

17. The circuit for measuring a bio-substance concentration of a biomaterial as claimed in claim 16, wherein said first transistor is an enzyme field-effect transistor.

18. The circuit for measuring a bio-substance concentration of a biomaterial as claimed in claim 16, wherein said second transistor is a reference field-effect transistor.

19. The circuit of claim 16, further comprised of said third transistor and said fourth transistor having the same-type channel as said first transistor.

20. The circuit for measuring a bio-substance concentration of a biomaterial as claimed in claim 16, wherein said first transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region of said first transistor and a channel having two ends extending in parallel with a surface of said ion sensitive membrane;

an enzyme sensitive membrane directly on the surface of said ion sensitive membrane over said gate region of said first transistor, for detecting said physical and chemical properties of a biomaterial of interest; and a second insulating layer on the surface of said first and second metal layers, for isolating said metal layers from said biomaterial of interest.

21. A circuit for measuring a bio-substance concentration of a biomaterial, comprising:

an enzyme field-effect transistor having an enzyme sensing membrane on a gate region, for sensing physical and chemical properties of a biomaterial of interest;

a reference field-effect transistor having a geometry and physical structure substantially identical to said enzyme field-effect transistor;

differential amplifier means comprised of at least two metal-oxide semiconductor field-effect transistors having a channel region of a conductivity type substantially identical to a respective channel region of said enzyme field-effect transistor and said reference field-effect transistor, for gain differentiating output signals of said enzyme field-effect transistor and said reference field-effect transistor; and single-ended converter means comprised of at least four metal-oxide semiconductor field-effect transistors, for providing a sensed signal representative of a bio-substance concentration of said biomaterial of interest in dependence upon reception of output signals of said differential amplifier means.

22. The circuit for measuring a bio-substance concentration of a biomaterial as claimed in claim 21, wherein said enzyme field-effect transistor comprises:

a P-type semiconductor substrate having first and second diffusion regions of a N-type material separated and spaced-apart by a gate region, said first and second diffusion regions respectively defining a source region and a drain region;

a first insulating layer positioned upon one surface of said P-type semiconductor substrate;

an ion sensitive membrane positioned upon one surface of said first insulating layer;

first and second metal layers formed in a V-shape, each of said first and said second layers having a base in contact with a center of one of said source region and said drain region and a channel having two ends extending parallel to a surface of said ion sensitive membrane;

enzyme sensitive membrane positioned directly upon one surface of said ion sensitive membrane over said gate region, for detecting said physical and chemical properties of said biomaterial of interest; and a second insulating layer positioned upon the surface of said first and second metal layers, for isolating said first and said second metal layers from said biomaterial of interest.

23. A method for measuring a bio-substance concentration of a biomaterial by the use of an enzyme FET having an enzyme sensing membrane on a gate region, and a reference FET having a geometry and physical structure substantially identical to said enzyme FET connected to a voltage source, said method comprising the steps of:

generating a sensed signal upon sensing physical and chemical properties of a biomaterial of interest by immersing said enzyme FET and said reference FET into said biomaterial of interest;

generating differential signals by gain differentiating said sensed signal to eliminate temperature dependency characteristics of said enzyme FET and said reference FET by a differential amplifier having at least two MOS-FETs having a channel region of a conductivity type substantially identical to a respective channel region of said enzyme FET and said reference FET to provide differential signals; and generating a measured signal representative of said bio-substance concentration of said biomaterial of interest in dependence upon said differential signals.

24. A method for measuring a bio-substance concentration of a biomaterial by the use of an enzyme FET having an enzyme sensing membrane on a gate region, and a reference FET having a geometry and physical structure substantially identical to said enzyme FET connected to a voltage source, said method comprising the steps of:

generating a sensed signal upon sensing physical and chemical properties of a biomaterial of interest by immersing said enzyme FET and said reference FET into said biomaterial of interest;

generating differential signals by gain differentiating said sensed signal to eliminate temperature dependency characteristics of said enzyme FET and said reference FET by a differential amplifier having at least two MOS-FETs having a channel region of a conductivity type substantially identical to a respective channel region of said enzyme FET and said reference FET to provide differential signals; and generating a measured signal representative of said bio-substance concentration of said biomaterial of interest by a single-ended converter in dependence upon said differential signals, said single-ended converter comprising at least four MOS-FETs having the channel of the conductivity type substantially identical to the respective channel of said enzyme FET and said reference FET.

25. The method as claimed in claim 24, wherein said enzyme field effect transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region and two ends extending in parallel with a surface of said ion sensitive membrane;

an enzyme sensitive membrane directly on the surface of said ion sensitive membrane over said gate region, for detecting physical and chemical properties of said biomaterial of interest; and a second insulating layer on the surface of said first and second metal layers, for isolating said metal layers from said biomaterial of interest.

26. A circuit for measuring a bio-substance concentration of a biomaterial, comprising:

a first transistor having a first electrode of a principal electrically conducting channel connected to a terminal for a first voltage source, a second electrode of said principal electrically conducting channel coupled to a first node and a common electrode formed with an enzyme sensing membrane for sensing physical and chemical properties of a biomaterial of interest;

a second transistor having a first electrode of a principal electrically conducting channel connected to said first terminal, a second electrode of said principal electrically conducting channel coupled to a second node and a common electrode disposed as a reference electrode;

a third transistor having a first electrode of a principal electrically conducting channel and a control electrode connected to a second terminal for a second voltage source and a second electrode of said principal electrically conducting channel coupled to said first node;

a fourth transistor having a first electrode of a principal electrically conducting channel and a control electrode connected to said second terminal and a second electrode of said principal electrically conducting channel coupled to said second node;

a fifth transistor having a first electrode of a principal electrically conducting channel connected to a third terminal for a third voltage source, a second electrode of said principal electrically conducting channel coupled to a third node and a control electrode coupled to said first node;

a sixth transistor having a first electrode of a principal electrically conducting channel connected to said third terminal, a second electrode of said principal electrically conducting channel coupled to an output terminal and a control electrode coupled to said second mode, for providing at said output terminal a measured signal representative of said bio-substance concentration of said biomaterial of interest;

a seventh transistor having a first electrode of a principal electrically conducting channel connected to a fourth terminal for a fourth voltage source and having a second electrode of said principal electrically conducting channel coupled to said third mode;

a eight transistor having a first electrode of a principal electrically conducting channel connected to said fourth terminal and having a second electrode of said principal electrically conducting channel coupled to said output terminal; and control electrodes of said seventh and eighth transistors being coupled to said third node.

27. The circuit of claim 26, further comprised of said third transistor and said fourth transistor having the same-type channel as said first transistor.

28. The circuit of claim 26, wherein said first transistor comprises:

a P-type semiconductor substrate having first and second diffusion regions of a N-type material separated and spaced-apart by a gate region, said first and second diffusion regions respectively representative of a source region and a drain region;

a first insulating layer on the surface of said P-type semiconductor substrate;

an ion sensitive membrane on the surface of said first insulating layer;

first and second metal layers in a V-shape, each having a base in contact at a center of one of said source region and said drain region of said first transistor and a channel having two ends extending in parallel with a surface of said ion sensitive membrane;

an enzyme sensitive membrane directly on the surface of said ion sensitive membrane over said gate region of said first transistor, for sensing said physical and chemical properties of said biomaterial of interest; and a second insulating layer on the surface of said first and second metal layers, for isolating said metal layers from said biomaterial of interest.

29. The circuit of claim 26 further comprising an aspect ratio of said seventh and eighth transistors to said third and fourth transistors providing a differential gain approaching unity.

* * * * *